(12) United States Patent
Matzger et al.

(10) Patent No.: US 8,222,179 B2
(45) Date of Patent: Jul. 17, 2012

(54) POROUS COORDINATION COPOLYMERS AND METHODS FOR THEIR PRODUCTION

(75) Inventors: Adam J. Matzger, Ann Arbor, MI (US); Antek G. Wong-Foy, Ann Arbor, MI (US); Kyoungmoo Koh, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/848,222

(22) Filed: Aug. 30, 2007

(65) Prior Publication Data
US 2009/0062409 A1    Mar. 5, 2009

(51) Int. Cl.
*B01J 20/22* (2006.01)
(52) U.S. Cl. ........ 502/401; 252/184; 502/152; 502/153; 502/154; 502/155; 502/156
(58) Field of Classification Search .......... 502/152–156, 502/401; 252/184
See application file for complete search history.

(56) References Cited

U.S. PATENT DOCUMENTS

| | | | |
|---|---|---|---|
| 3,197,436 A * | 7/1965 | Block et al. ................ 528/9 |
| 4,086,209 A | 4/1978 | Hara et al. | |
| 5,648,508 A | 7/1997 | Yaghi | |
| 6,617,467 B1 | 9/2003 | Mueller et al. | |
| 6,624,318 B1 | 9/2003 | Mueller et al. | |
| 6,756,195 B2 | 6/2004 | Weinberg et al. | |
| 6,893,564 B2 | 5/2005 | Mueller et al. | |
| 6,929,679 B2 | 8/2005 | Mueller et al. | |
| 6,930,193 B2 | 8/2005 | Yaghi et al. | |
| 7,008,607 B2 | 3/2006 | Mueller et al. | |
| 7,179,765 B2 | 2/2007 | Mueller et al. | |
| 7,196,210 B2 | 3/2007 | Yaghi et al. | |
| 7,202,385 B2 | 4/2007 | Mueller et al. | |
| 7,279,517 B2 | 10/2007 | Mueller et al. | |
| 7,309,380 B2 | 12/2007 | Mueller et al. | |
| 7,343,747 B2 | 3/2008 | Mueller et al. | |
| 7,411,081 B2 | 8/2008 | Mueller et al. | |
| 2003/0004364 A1 | 1/2003 | Yaghi et al. | |
| 2003/0078311 A1 | 4/2003 | Muller et al. | |
| 2003/0148165 A1 | 8/2003 | Muller et al. | |
| 2003/0222023 A1 | 12/2003 | Mueller et al. | |

(Continued)

FOREIGN PATENT DOCUMENTS
WO    WO2006125761    * 11/2006

OTHER PUBLICATIONS

Blue photoluminescent zinc coordination polymers with supertetranuclear cores, Tao et al, Chem. Commun., 2000, 2043-2044.*

(Continued)

*Primary Examiner* — Mark Kopec
*Assistant Examiner* — Haidung Nguyen
(74) *Attorney, Agent, or Firm* — Brooks Kushman P.C.

(57) ABSTRACT

A coordination polymer includes a plurality of metal atoms or metal clusters linked together by a plurality of organic linking ligands. Each linking ligand comprises a residue of a negatively charged polydentate ligand. Characteristically, the plurality of multidentate ligands include a first linking ligand having first hydrocarbon backbone and a second ligand having a second hydrocarbon backbone. The first hydrocarbon backbone is different than the second hydrocarbon backbone.

25 Claims, 6 Drawing Sheets

U.S. PATENT DOCUMENTS

| | | | |
|---|---|---|---|
| 2004/0081611 | A1 | 4/2004 | Muller et al. |
| 2004/0225134 | A1 | 11/2004 | Yaghi et al. |
| 2004/0249189 | A1 | 12/2004 | Mueller et al. |
| 2004/0265670 | A1 | 12/2004 | Mueller et al. |
| 2005/0004404 | A1 | 1/2005 | Mueller et al. |
| 2005/0124819 | A1 | 6/2005 | Yaghi et al. |
| 2005/0154222 | A1 | 7/2005 | Mueller et al. |
| 2005/0192175 | A1 | 9/2005 | Yaghi et al. |
| 2006/0057057 | A1 | 3/2006 | Mueller et al. |
| 2006/0089253 | A1 | 4/2006 | Mihan et al. |
| 2006/0135824 | A1 | 6/2006 | Mueller et al. |
| 2006/0154807 | A1 | 7/2006 | Yaghi et al. |
| 2006/0165995 | A1* | 7/2006 | Im et al. .......................... 428/408 |
| 2006/0185388 | A1 | 8/2006 | Mueller et al. |
| 2006/0252641 | A1 | 11/2006 | Yaghi et al. |
| 2006/0287190 | A1* | 12/2006 | Eddaoudi et al. .............. 502/60 |
| 2007/0068389 | A1 | 3/2007 | Yaghi |
| 2007/0202038 | A1 | 8/2007 | Yaghi et al. |
| 2008/0214806 | A1* | 9/2008 | Schubert et al. .............. 544/226 |
| 2009/0005243 | A1* | 1/2009 | Goddard et al. .............. 502/401 |
| 2009/0178558 | A1* | 7/2009 | Hupp et al. ....................... 95/96 |

OTHER PUBLICATIONS

Systhesis and characterization of the mixed ligand coordination polymer CPO-5, Kongshaug et al., Journal of Solid State Chemistry 17, 2003, 182-187.*

Hydrothermal synthesis of two new zinc coordination polymers with mixed ligands, Wu et al., Inorganic Chemistry Communications 4, 2001, 561-564.*

Hydrogen Storage in mesoporous coordination frameworks: Experiment and Molecular Simulation, Xiang et al., The Journal of Physical Chemistry Letters 113, 2009,15106-15109.*

Photoluminescent Metal-Organic Polymer Constructed from Trimetallic Clusters and Mixed Carboxylates, Chen et al., Inorganic Chemistry, 2003, 42, 944-946).*

Shin-Ichiro Noro et al., "A New Methane Adsorbent, Porous Coordination Polymer", Angew. Chem. Int. Ed. 2000, 39, No. 12, pp. 2081-2084.

Danil N. Dybtsev, et al., Rigid and Flexible: A Highly Porous metal-Organic Framework with Unusual Guest-Dependent Dynamic Behavior, Angew. Chem. Int. Ed. 2004, 43, pp. 5033-5036.

Danil N. Dybtsev, et al., "A Homochiral Metal-Organic Material with Permanent Porosity, Enantioselective Sorption Properties, and Catalytic Activity", Angew. Chem. Int. Ed. 2006, 45, pp. 916-920.

Ramanathan Vaidhyanathan, et al., "A Family of Nanoporous Materials Based on an Amino Acid Backbone", Angew. Chem. Int. Ed., 2006, 45, pp. 6495-6499.

Simon M. Humphrey, et al., "Porous Cobalt (II)—Organic Frameworks with Corrugated Walls: Structurally Robust Gas-Sorption Materials", Angew. Chem. Int. Ed. 2007, 46, 272-275.

Xin-Long Wang, et al., "An Unprecedented Eight-Connected Self-Penetrating Network basked on Pentanuclear Zinc Cluster Building Blocks", The Royal Society of Chemistry 2005, Chem. Commun., 2005, pp. 4789-4791.

Samadora Thushari et al., "Microporous Chiral metal Coordination Polymers: Hydrothermal Synthesis, Channel Engineering an dStability of Lanthanide Tartrates", The royal Society of Chemistry 2005, Chem. Commun., 2005, pp. 5515-5517.

Junhua Jia, et al., "Twelve-Connected Porous Metal—Organic Frameworks with High H2 Adsorption", The Royal Society of Chemistry 2007, Chem. Commun., 2007, pp. 840-842.

Wei Chen, et all., "Photoluminescent metal—Organic Polymer Constructed from Trimetallic Clusters and Mixed Carboxylates", Inorganic Chemistry, 2003, 42, pp. 944-946.

Partha Mahata, et al., "A New Series of Three-Dimensional Metal—Organic Framework, et al.", Inorganic Chemistry, 2007, 46, pp. 1250-1258.

International Search Report mailed Nov. 24, 2008, 2 pgs.

* cited by examiner

POROUS COORDINATION COPOLYMERS AND METHODS FOR THEIR PRODUCTION

STATEMENT REGARDING FEDERALLY SPONSORED RESEARCH OR DEVELOPMENT

The invention was made with Government support under Contract No. DE-FG26-04NT42121 awarded by the Department of Energy. The Government has certain rights to the invention.

BACKGROUND OF THE INVENTION

1. Field of the Invention

In at least one aspect, the present invention relates to the synthesis of coordination polymers formed from metal ions or clusters and organic ligands.

2. Background Art

The design, synthesis, characterization, and application of porous materials has broadly attracted both scientists and engineers due to the need to understand and control reactions or processes that occur in nanometer-sized spaces. This has a profound commercial impact because porous solids are widely used as sorbents in important applications such as molecule storage, separation and heterogeneous catalysis.

Historically, zeolites have played a central role in such fields. In contrast to structurally ambiguous porous materials such as activated carbons and glasses, zeolites are crystalline materials that have a very narrow pore size distribution. Zeolites, both natural (i.e. aluminosilicates) and synthetic (i.e. aluminophosphates) are important examples of microporous crystalline materials that consist of interconnected tunnels or cages resulting in cavities and pores that are uniform in size for a specific zeolite and thus can be utilized as molecular sieves where molecules small enough to fit into the pores are adsorbed but larger ones are not. The largest pore diameter in a zeolitic material is limited to about 13 Å. Using surfactants as structure directing agents or templates, mesoporous silicate/aluminosilicate materials have been synthesized with pores sizes that are tunable in the range of about 20 to 100 Å. Such materials do not display pores with size uniformity approaching natural zeolites and display non-uniform functionality on their inner surfaces.

Progress in the area of hybrid inorganic-organic materials has lead to the development of coordination compounds that now extend in 1-, 2-, or 3-dimensions. The term coordination polymer has been used to describe such compounds in which the backbones or frameworks of these materials are made by connecting metal ions or metal clusters (referred to as vertices of the framework) with organic ligands that when bridging multiple metal centers are commonly referred to as linkers or links. Other terms used to refer to coordination polymers include metal-organic frameworks ("MOFs"), porous coordination polymers ("PCPs"), nanoporous coordination frameworks, hybrid porous solids, and metallo-organic polymers. Rapid advances in the field have revealed that coordination polymers can be synthesized with porosity thereby constituting a new class of materials that are crystalline molecular sieves. The atomic structure of many coordination polymers can be determined by X-ray crystallography, thus the dimensions of the pores or channels can be determined with excellent certainty. The internal surface areas of some porous coordination materials are significantly greater than other porous materials. The pore sizes/shapes are highly tunable, and larger pore sizes can be synthesized when compared to known zeolites. Functionalization of the backbones or frameworks in these materials can be achieved by starting the synthesis with organic linkers with functional groups already installed or by post synthesis modification.

Mesoporous coordination polymers (pore size=2-50 nm) are considerably more rare than microporous coordination polymers (pore size <2 nm) in part because as the size of the organic linker increases, the structural integrity of the resulting coordination polymer may decrease. This can result in a collapse of the pore structure and a loss of crystallinity once the guest molecules (typically the solvent of synthesis and synthetic components or byproducts) are removed. Alternatively, interpenetration or catenation is sometimes observed which limits the formation of mesopores through partial pore occupation. To date few examples of crystalline mesoporous coordination polymers have been reported, and those that have, may be categorized according to the geometry of their mesopores. The first type have 1D mesoporous channels. In these materials porosity is derived mainly from the contribution of well-defined mesopores and these do not exhibit the outstanding surface areas of their microporous counterparts. The second type of crystalline mesoporous coordination polymers exhibit mesoporous behavior due to a network of cages found throughout the structure. These mesoporous cages are often restricted by small apertures or windows that prohibit very large molecules from accessing the space inside.

Against this prior art background, there is still a desire for novel multidentate ligands that are useful for constructing porous materials.

SUMMARY OF THE INVENTION

The present invention solves one or more problems of the prior art by providing a coordination polymer. The coordination polymer of this embodiment includes a plurality of metal atoms or metal clusters linked together by a plurality of organic linking ligands. Each linking ligand comprises a residue of a negatively charged polydentate ligand. Characteristically, the plurality of multidentate ligands includes a first linking ligand having first hydrocarbon backbone and a second ligand having a second hydrocarbon backbone. The first hydrocarbon backbone is different than the second hydrocarbon backbone.

DETAILED DESCRIPTION OF THE PREFERRED EMBODIMENT(S)

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. The description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application in their entirety to more fully describe the state of the art to which this invention pertains.

As used herein "linking ligand" means a chemical species (including neutral molecules and ions) that coordinate two or more metal atoms or metal clusters resulting in a predetermined separation, and the definition of void regions or channels in the framework that is produced. Examples include 4,4'-bipyridine (a neutral, multiple N-donor molecule) and benzene-1,4-dicarboxylate (a polycarboxylate anion).

As used herein "non-linking ligand" means a chemical species that is coordinated to a metal but does not link one metal cluster to another metal cluster.

As used herein "guest molecule" means any chemical species that resides within the void regions of an open framework solid. Examples include: molecules of the solvent that fill the void regions during the synthetic process, other molecules that are exchanged for the solvent such as during immersion (via diffusion) or after evacuation of the solvent molecules, such as gases in a sorption experiment.

As used herein "metal cluster" means any metal containing moiety present in a coordination polymer. This definition embracing single metal atoms or metal ions to groups of metals or metal ions that optionally include ligands or covalently bonded groups.

In an embodiment of the present invention, a coordination polymer having two or more different linking ligands is provided. These coordination polymers are useful for gas storage applications (e.g., hydrogen, carbon dioxide, carbon monoxide, and other absorbable species as set forth herein). These coordination polymers define a molecular framework. The coordination polymer of this embodiment includes a plurality of metal atoms or metal clusters linked together by a plurality of organic linking ligands. Each linking ligand comprises a residue of a negatively charged polydentate ligand. Characteristically, the plurality of multidentate ligands include a first linking ligand having first hydrocarbon backbone and a second ligand having a second hydrocarbon backbone. The first hydrocarbon backbone is different than the second hydrocarbon backbone. In this context, different includes instances when the first and second hydrocarbon backbones have different ring or straight chain structures, as well as, instances when the first and second hydrocarbon backbones have similar ring or straight chain structures but different substituents (i.e., substituted with different functional groups). Also included as being different in this It is understood that the first and/or second hydrocarbon backbone may have one or more atoms replaced by a heteroatom (e.g., N, O, S). Coordination polymers of the present embodiment typically exhibit 2- or 3-dimensional order.

In a variation of the present embodiment, each metal cluster of the coordination polymer includes one or more metal ions with the organic linking ligands partially or fully compensating charges of the metal ions. In a further refinement, each metal cluster includes a metal ion or metalloid ion having a metal selected from the group consisting of Group 1 through 16 metals of the IUPAC Periodic Table of the Elements including actinides, lanthanides, and combinations thereof. Specific examples of useful metal ions include, but are not limited to, the metal ion selected from the group consisting of $Mg^{2+}$, $Ca^{2+}$, $Sr^{2+}$, $Ba^{2+}$, $Sc^{3+}$, $Y^{3+}$, $Ti^{4+}$, $Zr^{4+}$, $H^+$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^+$, $Rh^{2+}$, $Rh^{3+}$, $Ir^+$, $Ir^{3+}$, $Ni^{2+}$, $Ni^+$, $Pd^{2+}$, $Pd^{4+}$, $Pt^{2+}$, $Pt^{4+}$, $Cu^{2+}$, $Cu^+$, $Ag^+$, $Au^+$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$, and $Bi^+$.

As set forth above, some variations of the present embodiment exhibit porosity. In one variation, the coordination polymer has a pore volume per gram of coordination polymer greater than about 0.1 $cm^3/g$.

The present invention embraces coordination polymers having at least two linking ligands that are different from each other. In one variation, each organic linking ligand is described by formula I:

$$X_nY \qquad\qquad I$$

wherein X is a functional group;

n is an integer that is equal or greater than 2; and

Y is a hydrocarbon group or a hydrocarbon group having one or more atoms replaced by a heteroatom. In a refinement of this variation, X is $CE_2^-$, $C(AR)_2^-$, $RC(=G)C=C(G^-)R$, or $R^1C(=ZR^2)C=C(ZR^{2-})R_1$; E is O, S, Se, or Te; Z is N, P, or As; R, $R^1$, $R^2$ are H, alkyl group, or aryl group; A is N, P, or As; and G is O, S, Se, or Te. Suitable examples for X include, but are not limited to, $CO_2^-$, $CS_2^-$, $ROPO_2^-$, $PO_3^{-2}$, $ROPO_3^-$, $PO_4^{-2}$, $ROAsO_2^-$, $AsO_3^{-2}$, $ROAsO_3^-$, $AsO_4^{-2}$, $SO_3^-$, $SO_4^-$, $SeO_3^-$, $SeO_4^-$, $TeO_3^-$, or $TeO_4^-$. In another refinement of the present variation, Y comprises a moiety selected from the group consisting of a monocyclic aromatic ring, a polycyclic aromatic ring, a monocyclic heteroaromatic ring, a polycyclic heteroaromatic ring, alkyl groups having from 1 to 10 carbons, and combinations thereof. In another refinement of the present variation, Y is alkyl, alkyl amine, aryl amine, aralkyl amine, alkyl aryl amine, or phenyl. In still another refinement of the variation, Y is a $C_{1-10}$ alkyl, a $C_{6-50}$ aromatic ring system, a $C_{3-50}$ heteroaromatic ring system, a $C_{6-24}$ aromatic ring system, or a $C_{4-24}$ heteroaromatic ring system.

In a variation of the present embodiment, a coordination polymer is provided. The coordination polymer of this embodiment includes a plurality of metal clusters and a plurality of polytopic organic linking ligands. The plurality of multidentate ligands includes a first linking ligand having a first length; and a second ligand having a second length. In this context, length refers to the distance in a multidentate ligand between two functional groups used for linking (for example X in formula I). This distance is taken from the center of mass of the function group (taken alone). In one variation, when a linking ligand has 3 or more X groups, the relevant distance is the maximum distance defined in this manner. In a refinement of the present invention, the first and second lengths differ by at least 1 angstrom. In another refinement, the first and second lengths differ by at least 4 angstroms. In a refinement of the present invention, the first and second lengths differ by at most 25 angstroms. In another refinement, the first and second lengths differ by at most 15 angstroms. In another refinement, the first and second lengths are each independently at least 2 angstroms. In another refinement, the first and second lengths are each independently at least 6 angstroms. In another refinement, the first and second lengths are each independently at most 30 angstroms. In another refinement, the first and second lengths are each independently at most 20 angstroms. In another refinement, the first and second lengths are each independently from about 4 to about 30 angstroms. In another refinement, the first and second lengths are each independently from about 4 to about 20 angstroms.

An example of a coordination polymer of the present embodiment is provided by the material described by formula II:

[(BDC)(BTB)$_{4/3}$]Zn$_4$O   II and derivatives thereof, wherein BDC is benzene-1,4-dicarboxylate and BTB is benzene-1,3,5-tribenzoate. Another example is provided by the material described by formula III:

[(T$^2$DC)(BTB)$_{4/3}$]Zn$_4$O   III and derivatives thereof, wherein T$^2$DC is thieno[3,2-b]thiophene-2,5-dicarboxylate and BTB is benzene-1,3,5-tribenzoate.

In a variation of the invention, the coordination polymers are characterized by having an average pore dimension from about 2 to 40 angstroms. In another variation, the coordination polymers are characterized by having an average pore dimension from about 5 to 30 angstroms. In still another variation, the coordination polymers are characterized by having an average pore dimension from about 8 to 20 angstroms. In yet another variation of the present invention, the coordination polymers are characterized by having surface area greater than about 2000 m$^2$/g as determined by the Langmuir method. In yet another variation of the present invention, the coordination polymers are characterized by having surface area from about 1000 to about 4000 m$^2$/g as determined by the Langmuir method.

In a refinement of the present embodiment, the coordination polymer further includes at least one non-linking ligand. Examples of useful non-linking ligands include, but are not limited to, oxide, peroxide, superoxide, hydroxide, sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, sulfide, hydrogen sulphate, selenide, selenate, hydrogen selenate, telluride, tellurate, hydrogen tellurate, nitride, phosphide, arsenide, arsenate, hydrogen arsenate, dihydrogen arsenate, antimonide, antimonate, hydrogen antimonate, dihydrogen antimonate, fluoride, boride, borate, hydrogen borate, perchlorate, chlorite, hypochlorite, perbromate, bromite, hypobromite, periodate, iodite, hypoiodite, and combinations thereof.

In yet another refinement, the metal cluster further includes at least one atom from the group consisting of N, P, As, Sb, Bi, O, S, Se, Te, F, Cl, Br, I. These atoms are anionic and balance the electric charge of the metal cluster.

In another refinement of the present embodiment, the coordination polymer further includes an adsorbed chemical species. Examples of useful adsorbed chemical species include, but are not limited to, ammonia, carbon dioxide, carbon monoxide, hydrogen, amines, methane, oxygen, argon, nitrogen, argon, organic dyes, polycyclic organic molecules, and combinations thereof.

In still another refinement of the present embodiment, the coordination polymer further includes one or more guest molecules occupying the space within the framework. Examples of guest molecules include, but are not limited to, solvents, gases, amines, organic compounds, coordination compounds, polymers, organic particles, organometallic particles, inorganic particles, and combinations thereof. More specific examples of guest molecules include, but are not limited to, small organic alkanes, arenes, ethers, haloalkanes, esters, amides, sulfides, sulfoxides, amines, ketones, aldehydes, alcohols, thiols, hydrogen, ammonia, methane, oxygen, nitrogen, argon, carbon monoxide, carbon dioxide, nitrous oxide, sulfur dioxide, sulfur trioxide, ethylene, acetylene, and combinations thereof.

In another embodiment of the present invention, a method for forming a coordination polymer set forth above is provided. The method comprises combining two or more polytopic organic linking ligand precursors with a metal ion containing composition in a solvent to form a reaction mixture. In a variation, the coordination polymer is formed by allowing the reactants to stand for a predetermined period of time. The two or more polytopic organic linking ligand precursors comprises a first linking ligand precursor including a first hydrocarbon backbone and a second linking ligand precursor including a second hydrocarbon backbone. The details of the linking ligands are set forth above.

In a variation of the present invention, the reaction mixture further comprises a solvent selected from the group consisting of formamides, sulfoxides, nitriles, esters, amines, ethers, ketones, aromatics, aliphatics, water, and combinations thereof. Specific examples of solvents include, but are not limited to, ammonia, hexane, benzene, toluene, xylene, chlorobenzene, nitrobenzene, naphthalene, thiophene, pyridine, acetone, 1,2-dichloroethane, methylenechloride, tetrahydrofuran, ethanolamine, triethylamine, N,N-dimethyl formamide, N,N-diethyl formamide, methanol, ethanol, propanol, alcohols, dimethylsulfoxide, chloroform, bromoform, dibromomethane, iodoform, diiodomethane, halogenated organic solvents, N,N-dimethylacetamide, N,N-diethylacetamide, 1-methyl-2-pyrrolidinone, amide solvents, methylpyridine, dimethylpyridine, diethylethe, and mixtures thereof. In another variation, the reaction mixture further comprises a guest molecule as set forth above. Typically, the solvent or a guest molecule from the polymeric material is removed from the reaction mixture after sufficient formation of the coordination polymer has occurred. Solvents can be removed by flow-through degassing or exposure of the material to reduced pressure.

In a variation of the present embodiment, non-isomorphic and isomorphic products can be obtained by combining ditopic and polytopic linkers, by combining ditopic and ditopic linkers, or by combining polytopic and polytopic linkers. An example of a non-isomorphic compound is the combination of benzene-1,4-dicarboxylic acid and 1,3,5-tris(4-carboxyphenyl)benzene. The details of this example are set forth below. As background, it is noted that in the presence of zinc nitrate tetrahydrate and diethylforamide ("DEF"), pure benzene-1,4-dicarboxylic acid reacts to generate a coordination polymer, the crystal structure analysis of which shows it to be a simple cubic net in the Fm-3m space group. Similarly, pure 1,3,5-tris(4-carboxyphenyl)benzene reacts to generate a coordination polymer which from its crystal structure analysis shows a "qom" net in the trigonal P31c space group. However, if benzene-1,4-dicarboxylic acid and 1,3,5-tris(4-carboxyphenyl)benzene are mixed together in the presence of a zinc salt, a new phase is formed. The product distribution can be controlled by the mole ratio of benzene-1,4-dicarboxylic acid to 1,3,5-tris(4-carboxyphenyl)benzene. Typical examples for generating isomorphic materials is the combination of BDC and functionalized BDC linkers such as 2-amino BDC, diamines, halides, dihalides and so forth. In case of isomorphic materials, the feed ratio of two linkers will influence the composition of the product.

The following examples illustrate the various embodiments of the present invention. Those skilled in the art will recognize many variations that are within the spirit of the present invention and scope of the claims.

EXAMPLES

1. Reaction of $H_2BDC$ and $H_3BTB$

Porous crystals are produced by heating various ratios of $H_2BDC$ (1,4-benzenedicarboxylic acid) and $H_3BTB$ (1,3,5-tris(4-carboxyphenyl)benzene) in the presence of excess $Zn(NO_3)_2 \cdot 4H_2O$ at 85° C. after 2 days. Three distinct crystalline phases are observed as the mole fraction of $H_3BTB$ is increased. At low $H_3BTB$ concentrations only MOF-5 crystals are formed, however at a mole ratio of 8:2 ($H_2BDC$: $H_3BTB$), a new needle-shaped phase is formed in the presence of MOF-5. Increasing the $H_3BTB$ concentration leads to exclusive formation of the needle-shaped phase that, by powder X-ray diffraction (XRD), is different from MOF-5 and MOF-177. A further increase of the $H_3BTB$ concentration results in MOF-177 forming as well. Finally, at $H_2BDC$: $H_3BTB$ mole ratios $\geq$4:6, MOF-177 is the first product to crystallize out of solution.

Figure 1:
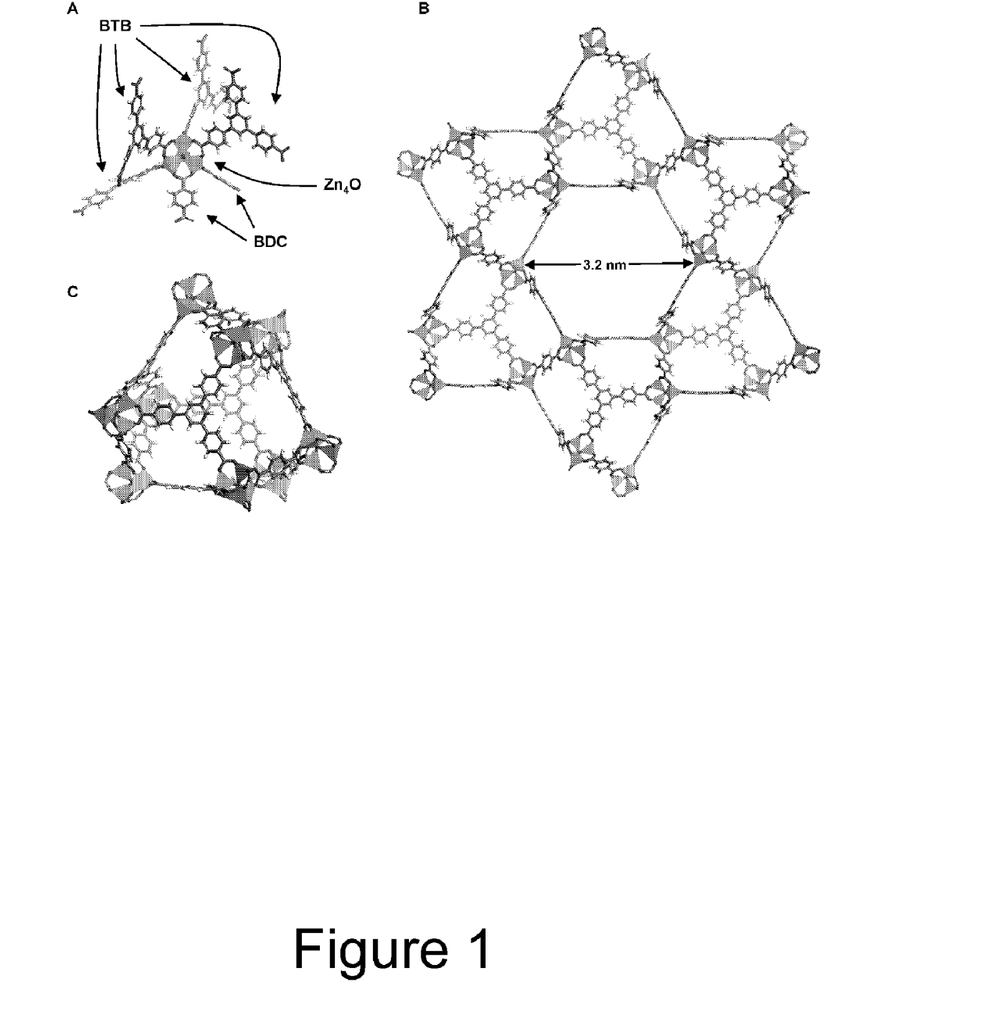
FIG. 1 provides the structure of UMCM-1. A. A Zn4O cluster coordinated to two BDC linkers and four BTB linkers. Zn4O clusters are shown as blue tetrahedra and C, H, and O atoms are shown as dark grey, white, and red, respectively. B. Structure of UMCM-1 viewed along the c-axis illustrating the one dimensional mesopore. C. A microporous cage constructed of six BDC linkers, five BTB linkers, and nine Zn4O clusters.

A single crystal X-ray diffraction study of the needle-shaped crystals revealed a structure with one dimensional hexagonal channel. The product crystallizes in the space group P63/m and dramatically differs from the structures derived from the pure linkers. The framework of the material consists of $Zn_4O$ clusters linked together by two BDC and four BTB linkers arranged in an octahedral geometry (FIG. 1A). Two BDC linkers are adjacent, leaving the other four positions occupied by BTB linkers. Analysis of the structure reveals it contains both micropores and mesopores. The micropores are found in cage-like structures constructed from six BDC linkers, five BTB linkers, and nine $Zn_4O$ clusters, with an the internal dimension of approximately 1.4 nm×1.7 nm (subtracting the van der Waals radii of the atoms, FIG. 1B). Six such microporous cages assemble together in an edge-sharing fashion to define the diameter of the mesopore, a 1D hexagonal channel 2.7 nm×3.2 nm (measured between pore walls, FIG. 1C). When van der Waals radii of the atoms are taken into account, the mesopore is 2.4 nm×2.9 nm. This product is denoted as UMCM-1 (University of Michigan Crystalline Material-1). Comparison of the bulk powder XRD pattern to the simulated pattern calculated from the single crystal data confirms that a single, phase-pure material is formed in the region where the mole ratio of $H_2BDC$: $H_3BTB$ is between 6:4 and 5:5. Elemental analysis of as-synthesized needles exchanged in $CH_2Cl_2$ and evacuated at room temperature supports the formulation of UMCM-1 as $Zn_4O(BDC)(BTB)_{4/3}$.

Figure 2:
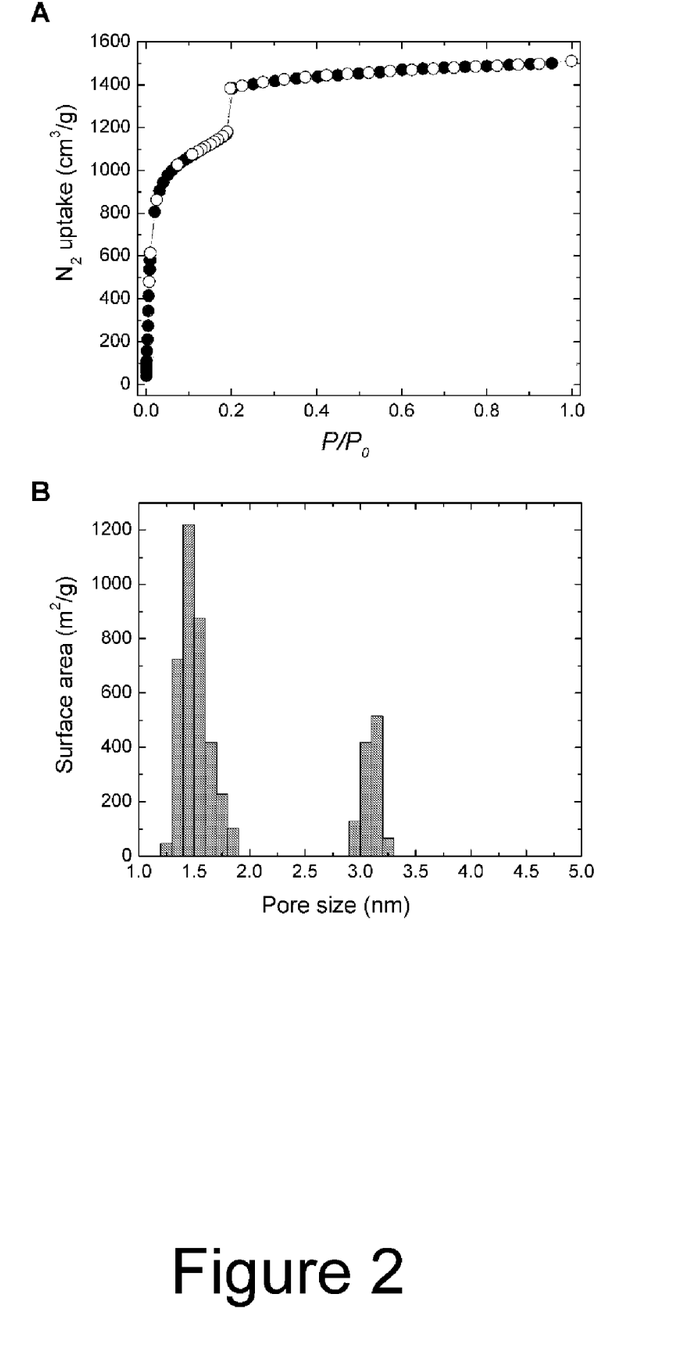
FIG. 2 provides: A. Nitrogen adsorption isotherm at 77 K for UMCM-1 (●, adsorption; ○, desorption) B. Pore size distribution calculated after fitting DFT models to Argon gas adsorption data at 87 K.
Figure 3:
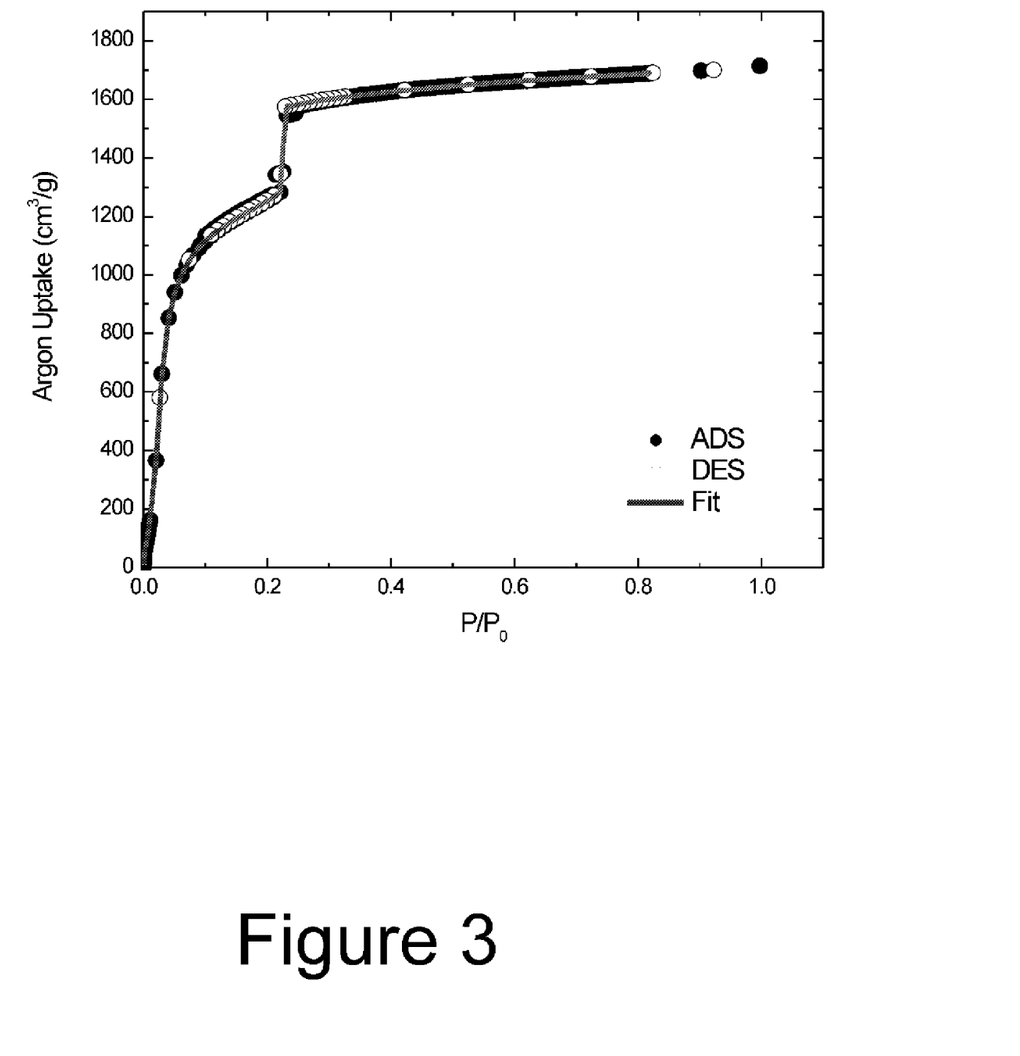
FIG. 3 provides Ar adsorption/desorption isotherm at 87 K for UMCM-1 and the corresponding NLDFT fit base on a cylindrical pore model.
Figure 4:
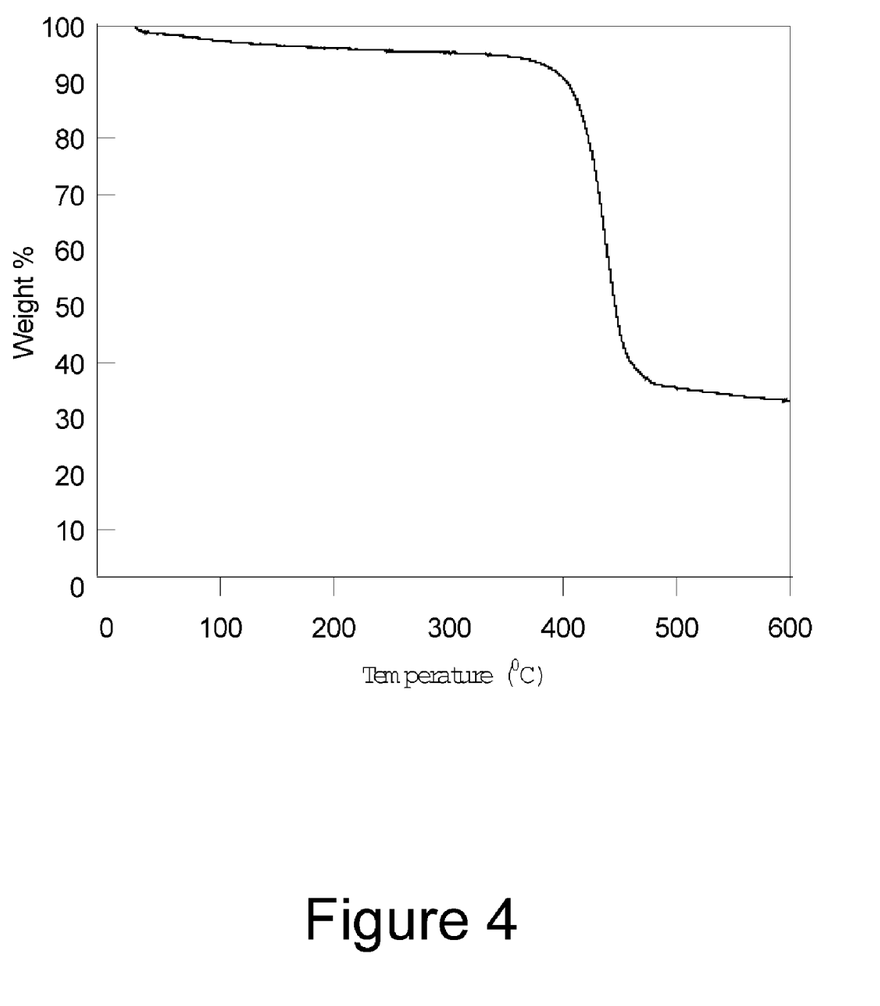
FIG. 4 provides a TGA trace of UMCM-1. Conditions: temperature ramp from 25° C. to 600° C. at 2° C./min under flow of N2 gas.
Figure 5:
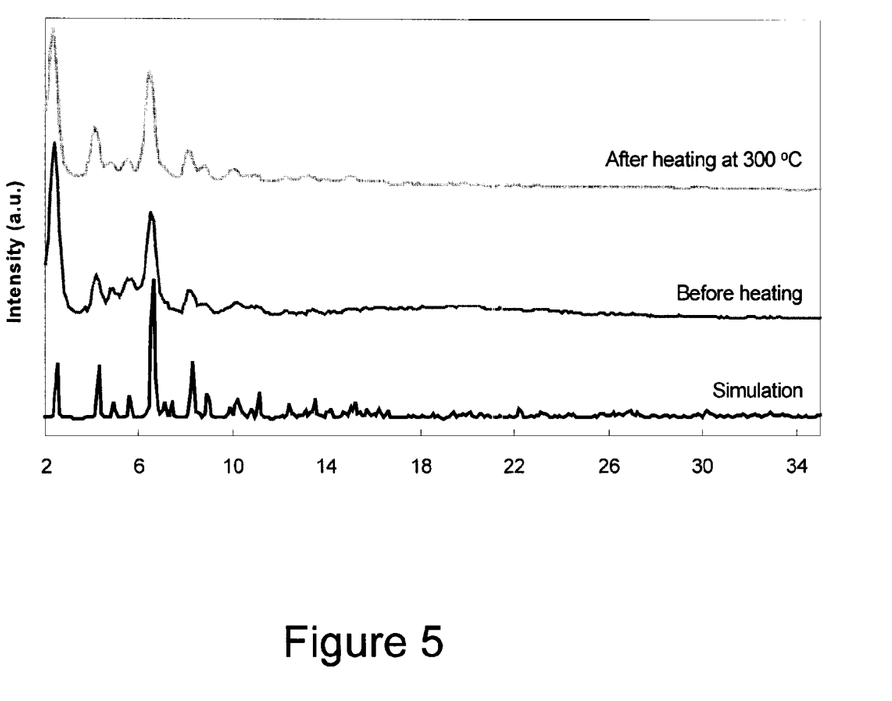
FIG. 5. Powder XRD pattern of UMCM-1 before and after heating at 300° C.
Figure 6:
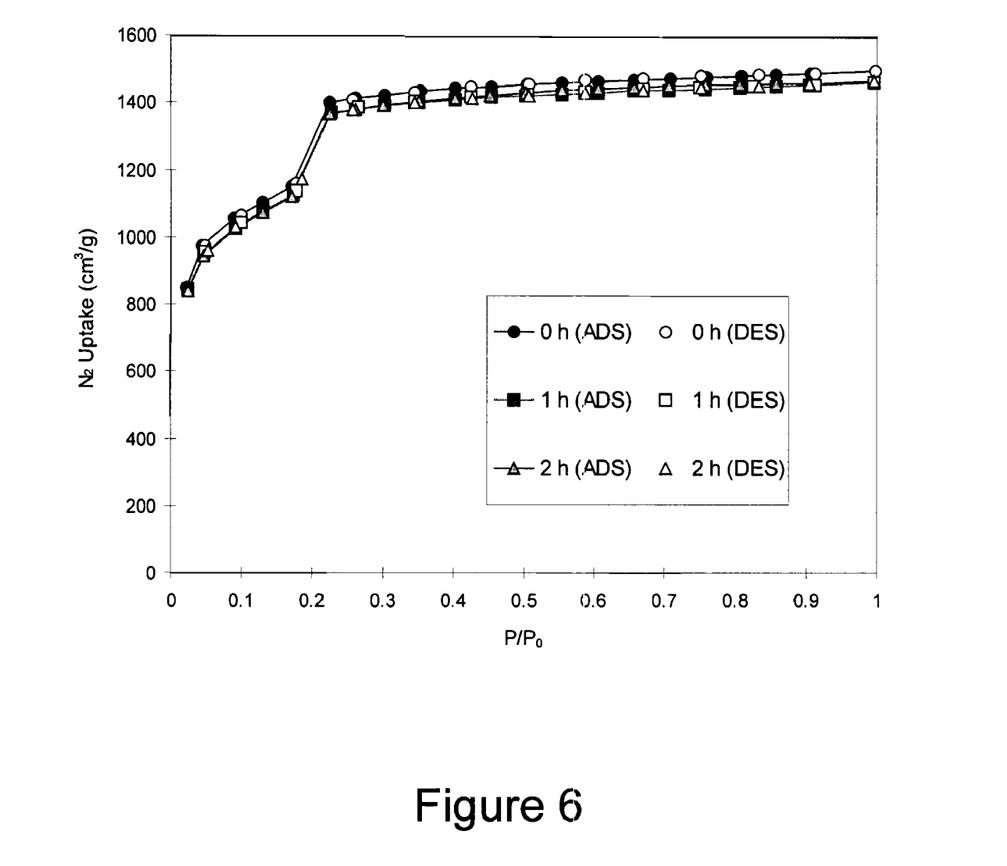
FIG. 6 provides N2 sorption isotherm of UMCM-1 after multiple heating and cooling cycles at 300° C.

The $N_2$ sorption isotherm of UMCM-1 is shown in FIG. 2A. From the distinctive step in the region $\sim P/P_0 = 0.2$, the isotherm can be classified as type IV. In striking contrast to other mesoporous channel examples however; UMCM-1 exhibits exceptionally high $N_2$ uptake ($\sim$1200 cm$^3$/g) up to the first plateau, indicative of a substantial microporous contribution to the sorption behavior. Assuming monolayer coverage of $N_2$ up to this first plateau and applying the Langmuir model, the apparent Langmuir surface area is calculated to be 4730 m$^2$/g (a similar treatment using the Brunauer-Emmer-Teller (BET) model affords a surface area of 4160 m$^2$/g). Taking the second plateau (>1400 cm$^3$/g) and applying the Langmuir model (12), the apparent surface area is calculated to be 6500 m$^2$/g; this value is significantly higher than that of any other material reported to date. A pore size distribution analysis of UMCM-1 by DFT methods (FIG. 2B) utilizing the Ar gas isotherm at 87 K (FIG. 3) reveals that there is a narrow distribution of micropores centered at about 1.4 nm and a narrow distribution of mesopores centered at about 3.1 nm, which is in excellent agreement with the results from crystallography (FIG. 1B). Advantageously, UMCM-1 exhibits properties of both microporous coordination polymers (ultra-high surface area) and mesoporous silicate/aluminosilicates (easily accessible mesopores). Although UMCM-1 achieves high levels of porosity, the structure is remarkably robust. TGA measurement recorded minimal weight loss up to 400° C. (FIG. 4 and no significant changes in the powder XRD pattern (FIG. 5). These measurements suggest no dramatic structural changes take place and indeed the $N_2$ sorption isotherm after heating to 300° C. for more than 3 hours is essentially unperturbed (FIG. 6), indicating that the framework of UMCM-1 is thermally stable.

Because UMCM-1 has large, accessible 1D channels, the potential for the material to serve as a host for large molecules is explored. Polycyclic dyes such as Nile red can readily diffused into the framework, and Reichardt's dye, a zwitterion which is unable to enter MOF-177 to an appreciable extent, rapidly dyes UMCM-1a light brown color. A more dramatic example of this is demonstrated by the incorporation of poly(3-hexylthiophene-2,5-diyl) (PHT, $M_n$=21,700, polydispersity index=2.18) into the mesopores of UMCM-1 from solution. The highly oriented pores can host and align regioregular PHT. The chain diameter of PHT (ca. 1.6 nm) leads chains to intercalate exclusively in the mesopores. The absorption spectrum of PHT in UMCM-1 shows marked linear dichroism, i.e., a change in the absorbance is observed with respect to a change in the axis of polarized light. This phenomenon is caused by the preferential alignment of anisotropic molecules and the results here provide strong evidence that PHT molecules are aligned along the main needle axis residing in the mesopores of UMCM-1. At 90° perpendicular to the axis of plane polarized light, the PHT impregnated crystals of UMCM-1 are yellow-orange; alignment with the axis of polarization results in a uniform color change to dark purple. This demonstrates, by far, the largest molecule absorbed into a coordination polymer to date and indicates an extremely high level of guest alignment.

2. Reaction of thieno[3,2-b]thiophene-2,5-dicarboxylic acid ($H_2T^2DC$) and $H_3BTB$ A second example of a non-isomorphic coordination polymer arises from the combination of thieno[3,2-b]thiophene-2,5-dicarboxylic acid ($H_2T^2DC$) and $H_3BTB$. At a ratio of 1:1 ($H_2T^2DC:H_3BTB$) a hexagonal plate-like phase is obtained. A single crystal X-ray diffraction study of these plates shows that the product crystallizes in the hexagonal space group. The framework of the material consists of $ZnO_4$ metal clusters linked together by two $T^2DCs$ and four BTBs arranged in an octahedral geometry. In this structure the $T^2DC$ links are disposed both opposite to each other as well as adjacent to each other leaving the other four positions occupied by BTB linkers. Analysis of the structure shows it has both micropores and mesopores. Pore size distribution analysis by DFT methods utilizing Ar gas at liquid Ar temperatures shows that there is a narrow distribution of micropores centered at 1.5 nm and a narrow distribution of mesopores centered at 2.5 nm. The product constructed with $T^2DCs$ and BTBs is denoted as UMCM-2. The $N_2$ uptake data of UMCM-2 shows that the isotherm can be classified as a type IV isotherm, indicating that the UMCM-2 contains mesopores. The BET surface area is 5100 $m^2/g$.

3. Reaction of BDC and ABDC

BDC and amino dicarboxylic acid ("ABDC") is combined with at feed ratio of 11:1 (mol BDC: ABDC) with 3 mol of Zinc nitrate tetrahydrate and DEF, the product ratio of BDC to ABDC was 12 to 1. The BET surface area (2690 $m^2/g$) of the product was between that of the pure compound made from BDC and Zinc nitrate (2720 $m^2/g$) and that of the compound made from ABDC and Zinc nitrate (2230 $m^2/g$).

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A coordination polymer comprising:
   a plurality of metal atoms or metal clusters, and
   a plurality of organic linking ligands, each linking ligand comprising residues of a negatively charged polydentate ligand, the plurality of multidentate ligands comprising:
   a first linking ligand having a first organic hydrocarbon backbone and a first length; and
   a second ligand having a second hydrocarbon backbone and a second length, the first hydrocarbon backbone being different than the second hydrocarbon backbone, the first and second lengths differing by at least 4 angstroms, wherein the coordination polymer exhibits 2- or 3-dimensional order and each metal cluster comprises one or more metal ions with the organic linking ligands partially or fully compensating charges of the metal ions and the first linking ligand and the second linking ligand are each independently described by formula I:

$$X_nY \qquad \text{I}$$

wherein X is a functional group;
n is an integer that is equal or greater than 2; and
Y is a hydrocarbon group or a hydrocarbon group having one or more atoms replaced by a heteroatom and wherein the coordination polymer has a pore volume per gram greater than about 0.1 $cm^3/g$.

2. The coordination polymer of claim 1 wherein each metal cluster comprises a metal ion or metalloid ion having a metal selected from the group consisting of Groups Ia to VIIIa metals, Groups Ib to VIIb, and combinations thereof.

3. The coordination polymer of claim 1 wherein the coordination polymer exhibits porosity.

4. The coordination polymer of claim 1 wherein:
X is $CE_2^-$, $C(AR)_2^-$, $RC(=G)C=C(G^-)R$, or $R^1C(=ZR^2)C=C(ZR^{2-})R_1$,
E is O, S, Se, Te;
Z is N, P, As;
R, $R^1$, $R^2$ are H, alkyl group, or aryl group;
A is N, P, As; and
G=O, S, Se, Te.

5. The coordination polymer of claim 1 wherein X is $CO_2^-$, $CS_2^-$, $ROPO_2^-$, $PO_3^{-2}$, $ROPO_3^-$, $PO_4^{-2}$, $ROAsO_2^-$, $AsO_3^{-2}$, $ROAsO_3^-$, $AsO_4^{-2}$, $SO_3^-$, $SO_4^-$, $SeO_3^-$, $SeO_4^-$, $TeO_3^-$, or $TeO_4^-$.

6. The coordination polymer of claim 1 wherein Y comprises a moiety selected from the group consisting of a monocyclic aromatic ring, a polycyclic aromatic ring, a monocyclic heteroaromatic ring, a polycyclic heteroaromatic ring, alkyl groups having from 1 to 10 carbons, and combinations thereof.

7. The coordination polymer of claim 1 wherein Y is alkyl, alkyl amine, aryl amine, aralkyl amine, alkyl aryl amine, or phenyl.

8. The coordination polymer of claim 5 wherein Y is a C1-10 alkyl, a $C_{1-10}$ alkyl amine, a $C_{7-15}$ aryl amine, a $C_{7-15}$ aralkyl amine, or a $C_{7-15}$ alkyl aryl amine.

9. The coordination polymer of claim 1 wherein the metal ion selected from the group consisting of $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{3+}$, $Rh^{2+}$, $Rh^+$, $Ir^{3+}$, $Ir^+$, $Ni^{2+}$, $Ni^+$, $Pd^{2+}$, $Pd^{4+}$, $Pt^{2+}$, $Pt^{4+}$, $Cu^{2+}$, $Cuer^+$, $Ag^+$, $Au^+$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$, and $Bi^+$.

10. The coordination polymer of claim 1 further comprising a non-linking ligand associated with the metal clusters.

11. The coordination polymer of claim 10 wherein the non-linking ligand is selected from the group consisting of $O^{2-}$, sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, sulfide, hydrogen sulphate, selenide, selenate, hydrogen selenate, telluride, tellurate, hydrogen tellurate, nitride, phosphide, arsenide, arsenate, hydrogen arsenate, dihydrogen arsenate, antimonide, antimonate, hydrogen antimonate, dihydrogen antimonate, fluoride, boride, borate, hydrogen borate, perchlorate, chlorite, hypochlorite, perbromate, bromite, hypobromite, periodate, iodite, hypoiodite; and mixtures thereof.

12. The coordination polymer of claim 1 further comprising an adsorbed chemical species.

13. The coordination polymer of claim 12 wherein the adsorbed chemical species is selected from the group consisting of ammonia, carbon dioxide, carbon monoxide, hydrogen, amines, methane, oxygen, argon, nitrogen, argon, organic dyes, polycyclic organic molecules, and combinations thereof.

14. The coordination polymer of claim 1 described by formula II:

$$[(BDC)(BTB)_{4/3}]Zn_4O \qquad II$$

and derivatives thereof,
wherein BDC is benzene-1,4-dicarboxylate and BTB is benzene-1,3,5-tribenzoate.

15. The coordination polymer of claim 1 described by formula III:

$$[(T^2DC)(BTB)_{4/3}]Zn_4O \qquad III$$

and derivatives thereof;
wherein $T^2DC$ is thieno[3,2-b]thiophene-2,5-dicarboxylate and BTB is benzene-1,3,5-tribenzoate.

16. A coordination polymer comprising:
a plurality of metal clusters, and
a plurality of polytopic organic linking ligands, the plurality of multidentate ligands comprising:
a first linking ligand having a first length; and
a second ligand having a second length, the first length being at least 1 angstroms greater than the second length wherein the first linking ligand and the second linking ligand are each independently described by formula I:

$$X_nY \qquad I$$

wherein X is a functional group;
n is an integer that is equal or greater than 2; and
Y is a hydrocarbon group or a hydrocarbon group having one or more atoms replaced by a heteroatom and wherein the coordination polymer has a pore volume per gram greater than about 0.1 cm$^3$/g.

17. A method for preparing a coordination polymer comprising:
a plurality of metal clusters, and
a plurality of residues derived from negatively charged linking ligands, the plurality of multidentate ligands comprising:
a first linking ligand having first hydrocarbon backbone and a first length; and
a second linking ligand having a second hydrocarbon backbone and a second length, the first hydrocarbon backbone being different than the second hydrocarbon backbone and the first and second lengths differing by at least 4 angstroms, wherein the coordination polymer exhibits 2- or 3-dimensional order and each metal cluster comprises one or more metal ions with the organic linking ligands partially or fully compensating charges of the metal ions, the method comprising:
a) combining two or more polytopic organic linking ligand precursors with a metal ion containing composition in a solvent to form a reaction mixture, the two or more polytopic organic linking ligand precursors comprising:
a first linking ligand precursor including the first organic backbone; and
a second linking ligand precursor including the second organic backbone wherein the first linking ligand and the second linking ligand are each independently described by formula I:

$$X_nY \qquad I$$

wherein X is a functional group;
n is an integer that is equal or greater than 2; and
Y is a hydrocarbon group or a hydrocarbon group having one or more atoms replaced by a heteroatom and wherein the coordination polymer has a pore volume per gram greater than about 0.1 cm$^3$/g.

18. The method of claim 17 wherein:
X is $CE_2^-$, $C(AR)_2^-$, $RC(=G)C=C(G^-)R$, or $R^1C(=ZR^2)C=C(ZR^{2-})R_1$,
E is O, S, Se, Te;
Z is N, P, As;
R, $R^1$, $R^2$ are H, alkyl group, or aryl group;
A is N, P, or As; and
G is O, S, Se, or Te.

19. The method of claim 18 wherein X is $CO_2^-$, $CS_2^-$, $ROPO_2^-$, $PO_3^{-2}$, $ROPO_3^-$, $PO_4^{-2}$, $ROAsO_2^-$, $AsO_3^{-2}$, $ROAsO_3^-$, $AsO_4^{-2}$, $SO_3^-$, $SO_4^-$, $SeO_3^-$, $SeO_4^-$, $TeO_3^-$, or $TeO_4^-$.

20. The method of claim 17 wherein the metal ion composition comprises a plurality of metal ions, corresponding counteranion, either free or as a component of a cluster, where the metal ions include a metal atom selected from the group consisting of metals from the elements of groups Ia, IIa, metals from the elements of groups IIIb to VIb; transition metal elements, groups IIIa to VIIIa including Lanthanides and Actinides, Groups Ib, IIb, and combinations thereof.

21. The method of claim 17 wherein the reaction mixture further comprises a solvent selected from the group consisting of formamides, sulfoxides, nitriles, esters, amines, ethers, ketones, aromatics, aliphatics, water, and combinations thereof.

22. The method of claim 17 wherein step a) is carried out by allowing the reactants to stand for a predetermined period of time.

23. The method of claim 17 further comprising:
b) removing the solvent or a guest molecule from the polymeric material.

24. The method of claim 23 wherein step b) comprises flow-through degassing or exposure of the material to reduced pressure.

25. The method of claim 17 wherein the solvent comprises a component selected from ammonia, hexane, benzene, toluene, xylene, chlorobenzene, nitrobenzene, naphthalene, thiophene, pyridine, acetone, 1,2-dichloroethane, methylenechloride, tetrahydrofuran, ethanolamine, triethylamine, N,N-dimethyl formamide, N,N-diethyl formamide, methanol, ethanol, propanol, alcohols, dimethylsulfoxide, chloroform, bromoform, dibromomethane, iodoform, diiodomethane, halogenated organic solvents, N,N-dimethylacetamide, N,N-diethylacetamide, 1-methyl-2-pyrrolidinone, amide solvents, methylpyridine, dimethylpyridine, diethylethe, and mixtures thereof.

* * * * *

UNITED STATES PATENT AND TRADEMARK OFFICE
CERTIFICATE OF CORRECTION

PATENT NO.        : 8,222,179 B2
APPLICATION NO.   : 11/848222
DATED             : July 17, 2012
INVENTOR(S)       : Adam J. Matzger et al.

It is certified that error appears in the above-identified patent and that said Letters Patent is hereby corrected as shown below:

Column 12, Line 21 Claim 18:

After "wherein X is $CO_2^-$" Delete "$CS_2$—" and insert -- $CS_2$- --.

Signed and Sealed this
Twenty-third Day of October, 2012

David J. Kappos
*Director of the United States Patent and Trademark Office*